United States Patent
Boudghene et al.

[11] Patent Number: 5,861,025
[45] Date of Patent: Jan. 19, 1999

[54] TUBULAR EXPANDABLE MEMBER FOR AN INTRALUMINAL ENDOPROSTHESIS, INTRALUMINAL ENDOPROSTHESIS, AND METHOD OF PRODUCTION

[75] Inventors: Frank Philippe Boudghene; Jean Baptiste Michel, both of Paris; Marc Robert Sapoval, Arcueil; Francois Lavaste, Saint Michel sur Orge, all of France

[73] Assignee: Assistance Publique Hopitaux De Paris, Paris, France

[21] Appl. No.: 624,551

[22] PCT Filed: Oct. 5, 1994

[86] PCT No.: PCT/FR94/01164

§ 371 Date: Jun. 20, 1996

§ 102(e) Date: Jun. 20, 1996

[87] PCT Pub. No.: WO95/09584

PCT Pub. Date: Apr. 13, 1995

[30] Foreign Application Priority Data

Oct. 5, 1993 [FR] France ................... 93/11854

[51] Int. Cl.⁶ ...................................................... A61F 2/06
[52] U.S. Cl. ................................................................ 623/1
[58] Field of Search ............................................. 623/1, 12

[56] References Cited

U.S. PATENT DOCUMENTS

| 3,657,744 | 4/1972 | Ersek. |
| 4,994,071 | 2/1991 | MacGregor ................... 623/1 |
| 5,360,443 | 11/1994 | Barone ......................... 623/1 |

FOREIGN PATENT DOCUMENTS

| 0274846A | 12/1987 | European Pat. Off. . |
| 0335341A1 | 3/1989 | European Pat. Off. . |
| 540290 | 5/1993 | European Pat. Off. ................. 623/12 |
| 8812719 | 10/1988 | Germany . |
| WO 95/09584 | 4/1995 | WIPO . |

*Primary Examiner*—Michael J. Milano
*Attorney, Agent, or Firm*—Jacobson, Price, Holman & Stern, PLLC

[57] ABSTRACT

Tubular expandable member for an intraluminal endoprosthesis, of the type comprising longitudinal portions linked successively in pairs by at least one transversal portion. The invention is characterized in that the transversal portion comprises at least one undulation which is deformable during expansion.

13 Claims, 3 Drawing Sheets

TUBULAR EXPANDABLE MEMBER FOR AN INTRALUMINAL ENDOPROSTHESIS, INTRALUMINAL ENDOPROSTHESIS, AND METHOD OF PRODUCTION

The present invention relates to a tubular expandable member for an endoprosthesis intended to be implanted in the lumen of a blood vessel, particularly for repairing narrowed or blocked blood vessels, such as the coronary arteries, the peripheral arteries or the renal arteries, or for treating aneurysms, particularly of the aorta in humans. It can also be used to treat stenoses or leakages in ducts other than vessels in the human body: bile ducts, urinary tract, airways, digestive tract, etc.

Experience has shown that an intraluminal endovascular prosthesis represents a possible alternative to conventional vascular surgery. The intraluminal endovascular prosthesis involves percutaneously inserting a tubular prosthetic graft, particularly of metal, into a blood vessel, and bringing it by way of a catheter towards the desired site inside the vascular system. The advantages of this method over conventional vascular surgery are that it is not necessary to perform surgical exposure, incision, removal, replacement or bypassing of the defective blood vessel.

The endoprostheses for the treatment of aneurysms comprise, in addition to the tubular member which has a fastening function, a textile covering which ensures the imperviousness of the new aorta.

The tubular metal fastening members (stents) are of three types: expandable, self-expanding, or with thermal shape memory.

The prostheses of the expandable type are the ones most used for the treatment of stenoses. They comprise a tubular expandable member made of metal on which is fixed, in the case of the endoprostheses intended for aneurysms, the textile covering.

The prosthesis is pressed onto the angioplasty balloon catheter and the whole assembly is introduced into a sheath. By retracting the sheath at the release site, the balloon is inflated and will create a plastic deformation of the prosthesis. Once implanted, the diameter of the prosthesis is the one which has been set, that is to say the diameter of the balloon catheter following inflation.

One of the major problems is associated with the size of the prosthesis. In the case of the human aorta, for example, the prosthesis, once it has been fitted in the lumen of the aorta, must have a diameter of the order of 20 mm, but it must not have a diameter any greater than 3 to 4 mm in the initial state, so that it can be introduced into the vessel and brought to the site in which it is to be placed.

There is therefore a need for tubular expandable members which can attain a final diameter of close to 20 mm, while at the same time having as small as possible a diameter in the initial state.

A tubular expandable member is known, especially from EP 0,364,787, which comprises slots formed in the wall of the tubular member and disposed substantially parallel to the longitudinal axis of the tubular member, each slot being uniformly separated from the adjoining slot, along a circumferential axis, by transverse connection pieces, in such a way as to form longitudinal tube portions established between successive slots. The ends of each slot are disposed in intermediate fashion in relation to the adjoining slot in such a way that the transverse connection pieces disposed at the end of each slot and between the longitudinal portions are in turn disposed in intermediate fashion in relation to the two ends of the adjoining slot, the adjoining slots thereby being disposed in a staggered manner in relation to one another. The longitudinal portions have a width which is substantially identical to that of the transverse connection pieces, so that when the prosthesis is put into place, a deformation of the longitudinal portions takes place essentially in the part situated between two successive transverse connection pieces along the longitudinal axis, providing the tubular member with diamond-shaped openings upon completion of the dilation.

The disadvantages of such a tubular member are a lack of longitudinal flexibility, a reduction in the final length, after positioning, compared to the initial length, and difficulties of crimping on the balloon for dilation and widening.

The object of the present invention is to provide a tubular expandable member for an intraluminal endoprosthesis which does not have the disadvantages of the prior art and which takes up as little space as possible in the initial state.

The subject of the invention is therefore a tubular expandable member for an intraluminal endoprosthesis, of the type which is obtained by cutting from a tube and which can be expanded by application of force, comprising longitudinal portions which are connected in pairs successively by at least one transverse portion, in which the said transverse portion comprises at least one undulation which is deformable during expansion of the member.

According to the invention, the tubular member has a constant length determined by the said longitudinal portions, and the deformable undulation is provided in such a way that the deformation of the transverse portions has an effect exclusively on the radial dimension of the tubular member.

The tubular member advantageously comprises a transverse connection portion at each end of the longitudinal portions. The transverse connection portions are preferably disposed symmetrically. According to a preferred embodiment, the transverse connection portions are disposed in line with one another.

Alternatively, the tubular member according to the invention comprises at least one transverse connection portion disposed in the intermediate part of the longitudinal portions.

The undulations are advantageously in the general shape of a U, the ends of the sides of the U being joined to the longitudinal portions of the member.

The longitudinal portions and the transverse portions advantageously have the same thickness, and the longitudinal portions have a width which is greater than the width of the transverse portions, preferably at least equal to twice the width of the transverse portions.

According to another embodiment of the invention, the successive longitudinal portions comprise projecting reinforcement parts in line with one another.

The tubular member is made of metal, preferably stainless steel.

The tubular member according to the invention can be used such as it is in order to form an intraluminal prosthesis for the treatment of stenoses by means of intraluminal expansion.

It can also be used for the treatment of aneurysms by means of an expandable intraluminal endoprosthesis, where it will form the central part, with a peripheral sheath made of an impervious material then being fixed to the tubular member, and this sheath advantageously being made of woven polyester fibres, preferably Dacron®.

The invention also relates to a method of producing a tubular member as described hereinabove, characterized in that longitudinal portions and transverse portions are cut by laser from a hollow tube having a diameter and a wall thickness identical to the diameter and wall thickness of the final tubular member.

The invention will be described in detail hereinafter with reference to the attached figures, in which.

Figure 1:
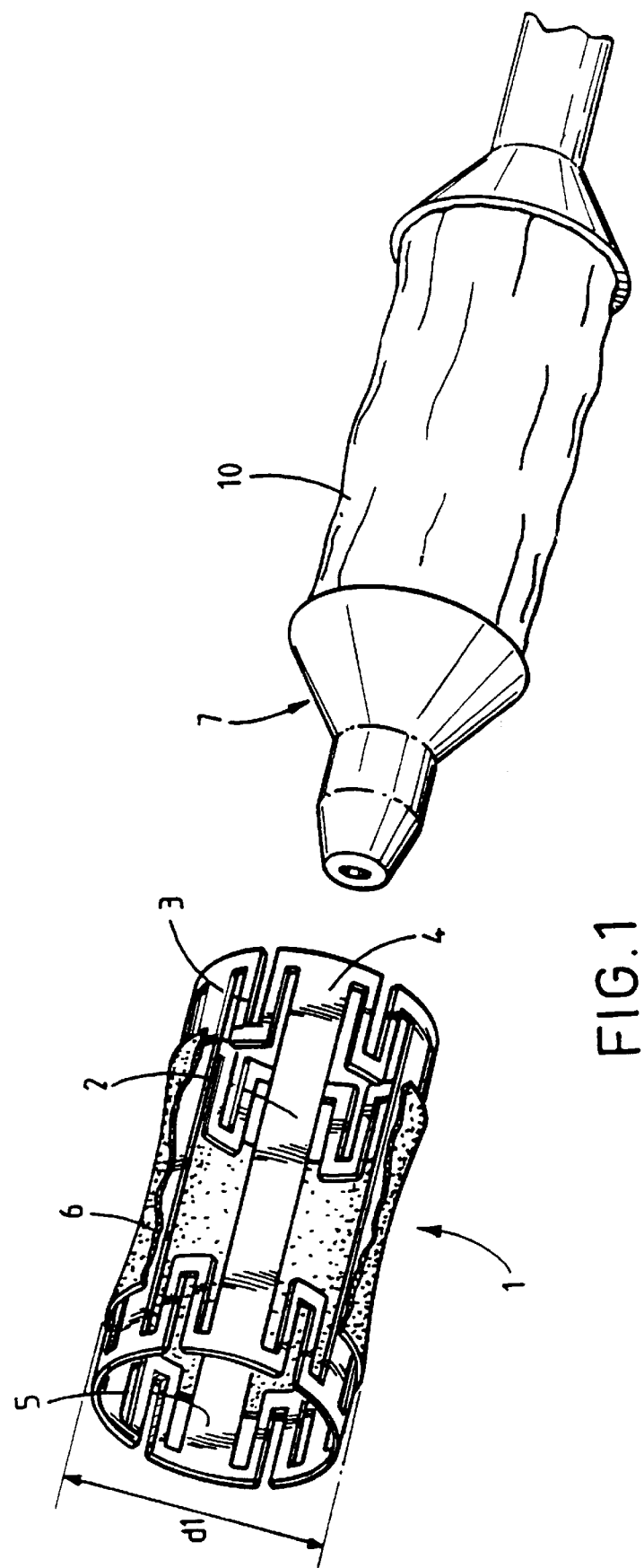
FIG. 1 represents a perspective view, with partial sectioning, of a vascular endoprosthesis according to the invention, comprising a first embodiment of a tubular expandable member and a peripheral sheath.

FIG. 1 represents a vascular endoprosthesis of the type intended to treat aneurysms, in the initial state, comprising a tubular member 1 whose wall comprises longitudinal parts 2 and U-shaped transverse portions 3 serving as connection elements between two successive longitudinal portions and disposed at the ends 4 and 5 of each longitudinal portion 2.

A sheath 6 made of woven polyester is fixed on this tubular member 1. The woven polyester sheath 6 is fixed to the tubular member 1 by stitching at separate points between the metal elements of the tubular member and the textile of the sheath 6. The sheath 6 has a length which is smaller than the tubular member 1, in such a way that the tubular member 1 protrudes by about 10 mm at each end, as is represented in FIG. 1.

The vascular endoprosthesis represented in FIG. 1 is crimped on a catheter 7 with angioplasty balloon 10, here represented in the non-inflated state.

Figure 2:
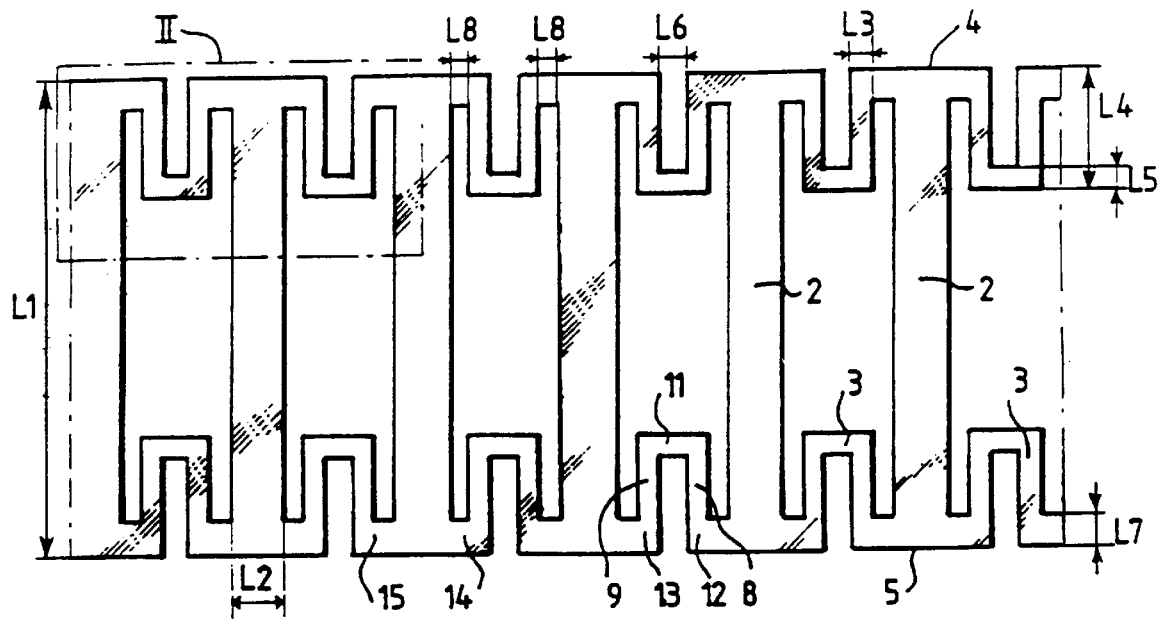
FIG. 2 represents a plan view of the unrolled configuration of the tubular expandable member which is represented in FIG. 1.

As is represented in FIG. 2, the tubular member comprises six parallel longitudinal portions 2 oriented along the longitudinal axis of the tubular member.

Each longitudinal portion 2 is joined via its ends 4 and 5 to the adjoining longitudinal portion 2 by way of a transverse portion 3 having the shape of a U whose side branches 8 and 9 are joined to each other by an intermediate branch 11. The ends 12 and 13 of the side branches of the U-shaped transverse portion 3 are joined to the ends 4 and 5 of longitudinal portions 2 by means of joining segments 14 and 15.

The tubular member which is represented in FIG. 1 has the following dimensions:

diameter ($d_1$) of the tubular element: 3 mm
thickness of the wall of the tubular element: 0.3 mm
$L_1$: length of the tubular member: 60 mm
$L_2$: width of the longitudinal portions 2: 0.79 mm
$L_3$: width of the side branches 8 and 9 of the U-shaped transverse portion 3: 0.2 mm
$L_4$: length of the side branches 8 and 9 of the U-shaped transverse portion 3: 4.7 mm
$L_5$: length of the intermediate branch 11: 0.25 mm
$L_6$: width of the intermediate branch 11: 0.125 mm
$L_7$: length of the joining segments 14 and 15: 0.25 mm
$L_8$: width of joining segments 14 and 15: 0.125 mm The above-described construction of the prosthesis allows the latter to be expanded in a uniform manner and outwards, and in a controlled manner in order to convert to the configuration represented in FIG. 1 or 2, upon application of a suitable force, from the inside of the tubular member 1, as is described hereinbelow in greater detail.

The catheter 7 and the prosthesis formed by the tubular expandable member 1 and the polyester sheath 6 are brought in a conventional manner to the desired site, in order to expand the lumen of the duct in the body at the point where it is desired to implant the prosthesis. Fluoroscopy, ultrasound or other conventional techniques can be used to ascertain that the catheter and the prosthesis have been brought to the desired site inside the duct in the body. The prosthesis is then expanded and deformed in a controlled manner, by dilating the angioplasty balloon 10 of the catheter 7 in a controlled manner, in such a way that the prosthesis is expanded and deformed radially outwards, so as to come into contact with the duct in the body. When the desired expansion and deformation of the prosthesis have been accomplished, the angioplasty balloon can be collapsed or deflated and the catheter 7 can be removed in a conventional manner from the duct in the body. If so desired, the catheter 7 and the prosthesis can be initially surrounded by a conventional Teflon sheath, which is removed from the prosthesis before the latter is expanded.

The tubular member of the prosthesis initially has the first collapsed and predetermined diameter $d_1$, as is described in connection with FIGS. 1 and 2, in order to permit the insertion of the tubular member 1 into the duct in the body, as is described hereinabove. When it is desired to implant the prosthesis inside a duct in the body, the prosthesis is expanded and deformed in a controlled manner towards a second diameter $d_2$, the latter being variable and determined by the internal diameter of the duct in the body and by the amplitude of the expansion of the inflatable angioplasty balloon 10 of the catheter 7. Correspondingly, the expanded and deformed prosthesis, upon inflation of the angioplasty balloon 10, will not be able to migrate from the desired site, inside the duct in the body, and, analogously, the expansion of the prosthesis will not be able to cause rupturing of the duct in the body. In addition, insofar as the prosthesis is not "elastic" or a "self-expanding member", the prosthesis does not apply in a continuous manner a radial force, directed outwards against the inner surface of the duct in the body, which exceeds the force necessary to withstand a radial collapse of the duct in the body. Thus, the erosion of the inner surface or tunica intima of the artery or duct in the body is prevented.

When it is desired to use the tubular expandable intraluminal member to dilate the lumen of a duct in the body presenting a stenosed area, the expansion of the intraluminal tubular member 1 with the aid of the angioplasty balloon 10 permits a controlled dilation of the stenosed area and at the same time a controlled expansion and deformation of the vascular endoprosthesis formed by the tubular expandable member 1 such that the latter prevents the duct in the body from collapsing and reducing the size of the lumen expanded beforehand. Once again, the second expanded diameter of the intraluminal endoprosthesis is variable and is determined by the desired expanded internal diameter of the duct in the body. Thus, the expandable intraluminal endoprosthesis will not migrate from the desired site inside the duct in the body upon deflation of the angioplasty balloon, and, analogously, the expansion of the intraluminal endoprosthesis will cause neither rupturing of the duct in the body nor erosion. In addition, if an intimal flap or fissure were to form in the duct in the body, at the position of the endoprosthesis, the latter will ensure that this intimal flap cannot bend inwards, in the duct in the body, nor become detached by being torn off and circulate through the duct in the body. In the case where the endoprosthesis is used to expand the lumen in a critical duct area in the body, such as the main left coronary artery, the intimal flap will not be able to block the main left coronary artery of the heart or cause the death of the patient.

Figure 3:
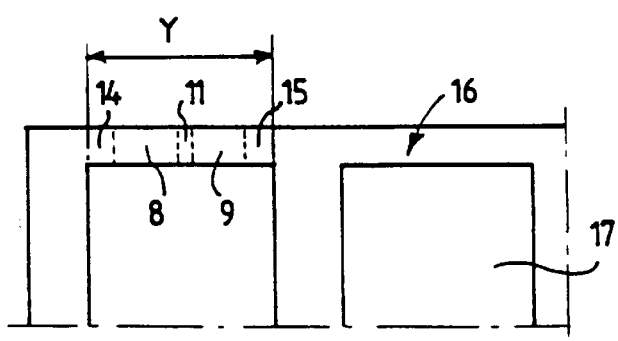
FIG. 3 represents a plan view of the framed area II in FIG. 2 after expansion of the tubular member by dilation.

FIG. 3 represents the tubular element 1 in FIG. 2 in the theoretical expanded state after dilation by the angioplasty balloon 10, as is represented in FIG. 1. The side branches 8, 9 and the intermediate branch 11 of the U, when fully deployed, form, together with the joining segments 14 and 15, a rectilinear portion 16 of length Y joining each successive longitudinal element 2 in such a way that the tubular element 1 is in the general shape of a tube whose wall is made up of longitudinal portions 2 and slots 17 of substantially rectangular shape.

After expansion, the dimensions of the tubular element are:

$d_2$: diameter of the tubular element: ≅20 mm
$L_2$: length of the tubular element: 60 mm
Y≅9.21 mm.

In practice, it is possible for the tubular element not to be expanded completely. Variations in expansion are even desirable (within a limited range) so that the final dimensions of the tube after dilation correspond exactly to the dimensions of the vessel where it is implanted (varying for each patient).

The tubular member 1 can be of any suitable material whatsoever which is compatible with the human body and the body fluids with which the vascular prosthesis may come into contact.

The tubular member 1 must also be made of a material which has the strength and elasticity characteristics necessary to permit the tubular member 1 to be expanded and deformed from the configuration represented in FIG. 2 to the configuration represented in FIG. 3, and in addition to permit the tubular member 1 to maintain its expanded and deformed configuration with the increased diameter $d_2$ corresponding to the state represented in FIG. 3 and to withstand a radial collapse. Suitable materials for the manufacture of the tubular member 1 include silver, tantalum, stainless steel, gold, titanium or any other suitable synthetic material having the requisite characteristics which have been described above.

The tubular member 1 is preferably initially a stainless steel tube, with a thin wall, having a uniform wall thickness, a particularly preferred material being stainless steel 316L.

The tubular member 1 represented in FIG. 2 has been obtained by cutting a stainless steel tube having a diameter of 3 mm, and a wall thickness of 0.3 mm, using a YAG laser whose parameters are as follows:

Frequency = 196 Hz
Pulse width = 0.6 MS      Energy = 0.4 Joules
Current = 3 KV
Linear speed = 0.3 mm/min
Focal length = 80 mm Telescope—diameter of beam=1/10 mm
Gas—oxygen at 3 bar.

The apparatus used was equipped with a "microcontrol" table with dimensions:

X axis=250 mm
Y axis=200 mm.

The table was controlled by step motors of 5 μm increments.

To produce the components, a turntable equipped with a dead centre was used.

Cutting was inspected visually by magnifying glass.

Figure 4:
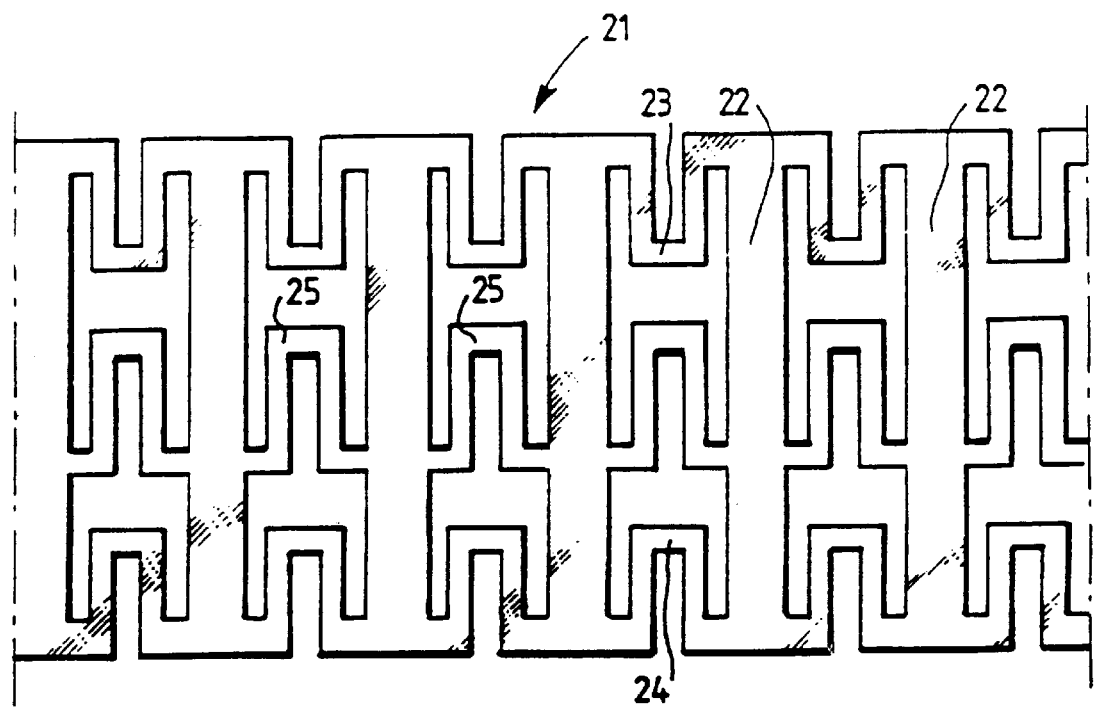
FIG. 4 represents a plan view of the unrolled configuration of the tubular member according to a second embodiment.

FIG. 4 represents the cutting of a second embodiment of the tubular member according to the invention.

In this embodiment, the tubular device 21 comprises longitudinal portions 22, of which there are six, and transverse portions 23 and 24, of which there are 12, disposed at the ends of the tubular member and joining in pairs the successive longitudinal portions which have a shape and arrangement substantially identical to those of the tubular member 1 described in FIGS. 1 to 3, the transverse portions 23 being disposed at one of the ends of the tubular member 21, and the transverse portions 24 at the other end.

In this embodiment, the tubular member 21 also comprises transverse connection portions 25 disposed in the intermediate part of the longitudinal portions 22, in a symmetrical manner both in the direction of the transverse portions 23 of one of the ends and in the direction away from the transverse portions 24 of the other end of the tubular member 21.

The dimensions of the various elements are substantially the same as the dimensions indicated for the various elements of the tubular member which is represented in FIGS. 1 to 3.

In an alternative of this embodiment, which has not been represented, the tubular member 21 comprises 8 longitudinal portions, instead of 6, which are joined in pairs at each end by transverse portions 23 and 24 and in their intermediate part by transverse portions 25 whose configuration and dimensions are substantially the same as those of the transverse portions represented in FIG. 4. In this case, the longitudinal portions have a width of about 0.4 mm.

Figure 5:
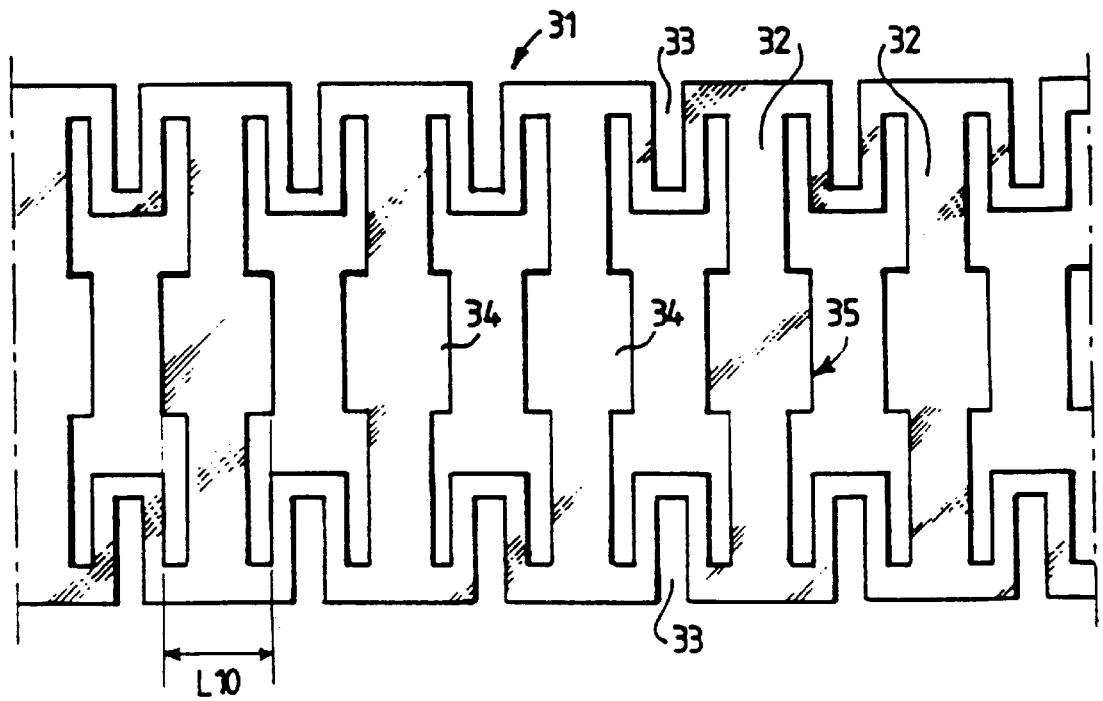
FIG. 5 represents a plan view of the unrolled configuration of the tubular member according to a third embodiment.

In the embodiment represented in FIG. 5, the tubular member 31 comprises longitudinal portions 32 and transverse portions 33 disposed at each end of the longitudinal portions 32 and connecting each longitudinal portion 32 to the directly adjoining longitudinal portion 32, having an arrangement and dimensions substantially identical to those of the transverse portions represented in FIGS. 2 and 3.

The successive longitudinal portions 32 comprise projecting reinforcing parts 34 disposed in line with one another in the intermediate part 35 of the longitudinal portions 32. In this embodiment, the intermediate part of each longitudinal portion has a width $L_{10}$ of 1.2 mm, the dimensions of the other elements, including the ends of the longitudinal parts 32, being otherwise substantially identical to those of the tubular member which is represented in FIG. 2.

The dimensions indicated for FIGS. 1 to 4 are dimensions which are adapted to the use of the intraluminal endoprosthesis for the treatment of aortic aneurysms.

It goes without saying that the dimensions can be easily determined by the person skilled in the art on the basis of the above description for adapting an endoprosthesis according to the invention to the treatment of aneurysms or treatment of stenoses in other vessels or ducts of smaller diameter.

Finally, the textile or synthetic part which provides for the imperviousness can be attached at a variable height on the metal part.

We claim:

1. Tubular member (1) for an intraluminal endoprosthesis, of the type which is obtained by cutting from a tube and which can be expanded by application of a force, comprising longitudinal portions (2, 22, 32) which are connected in pairs successively by at least one transverse portion (3, 23, 33) having the same thickness as the longitudinal portions and a width less than the longitudinal portions, characterized in that the said transverse portion comprises at least one undulation which is deformable during expansion of the member, this deformable undulation being provided in such a way that the deformation of the transverse portions has an effect exclusively on the radial dimension of the tubular member.

2. Tubular member according to claim 1, characterized in that it comprises a transverse connection portion (3, 23, 33) at each end of the longitudinal portions.

3. Tubular member according to claim 1, characterized in that it comprises transverse connection portions (3, 23, 33) which are disposed symmetrically.

4. Tubular member according to claim 1, characterized in that it comprises transverse connection portions (3, 23, 33) which are disposed in line with one another.

5. Tubular member according to claim 1, characterized in that it comprises at least one transverse connection portion (3, 23, 33) which is disposed in the intermediate part of the longitudinal portions.

6. Tubular member according to claim 1, characterized in that the undulations are in the general shape of a U, in which one of the ends of a different one of the side branches (8 and 9) is joined to each end of the longitudinal portions (2, 22, 32) of the member.

7. Tubular member according to claim 1, characterized in that the longitudinal portions (2, 22, 32) have a width substantially equal to at least twice the width of the transverse portions (3, 23, 33).

8. Tubular member according to claim 1, characterized in that the successive longitudinal portions (32) comprise projecting reinforcing parts (34) in line with one another.

9. Tubular member according to claim 1, characterized in that it is made of stainless steel.

10. Expandable intraluminal endoprosthesis for the treatment of stenoses, characterized in that it comprises a tubular member (1) for an intraluminal endoprosthesis, of the type which is obtained by cutting from a tube and which can be expanded by application of a force, comprising longitudinal portions (2, 22, 32) which are connected in pairs successively by at least one transverse portion (3, 23, 33) having the same thickness as the longitudinal portions and a width less than the longitudinal portions, characterized in that the said transverse portion comprises at least one undulation which is deformable during expansion of the member, this deformable undulation being provided in such a way that the deformation of the transverse portions has an effect exclusively on the radial dimension of the tubular member.

11. Intraluminal vascular endoprosthesis in particular for the treatment of aneurysms, characterized in that it comprises a central part formed by a tubular expandable member (1) for an intraluminal endoprosthesis, of the type which is obtained by cutting from a tube and which can be expanded by application of a force, comprising longitudinal portions (2, 22, 32) which are connected in pairs successively by at least one transverse portion (3, 23, 33) having the same thickness as the longitudinal portions and a width less than the longitudinal portions, characterized in that the said transverse portion comprises at least one undulation which is deformable during expansion of the member, this deformable undulation being provided in such a way that the deformation of the transverse portions has an effect exclusively on the radial dimension of the tubular member and a peripheral part formed by a sheath (6).

12. Intraluminal endoprosthesis according to claim 11, characterized in that the sheath is made up of woven polyester fibers.

13. Method of producing a tubular member (1) for an intraluminal endoprosthesis, of the type which is obtained by cutting from a tube and which can be expanded by application of a force, comprising longitudinal portions (2, 22, 32) which are connected in pairs successively by at least one transverse portion (3, 23, 33) having the same thickness as the longitudinal portions and a width less than the longitudinal portions, characterized in that the said transverse portion comprises at least one undulation which is deformable during expansion of the member, this deformable undulation being provided in such a way that the deformation of the transverse portions has an effect exclusively on the radial dimension of the tubular member comprising cutting a hollow tube to produce longitudinal portions (2, 22, 32) and transverse portions (3, 23, 33).

* * * * *